United States Patent [19]
Mishra et al.

[11] Patent Number: 5,441,481
[45] Date of Patent: Aug. 15, 1995

[54] MICRODIALYSIS PROBES AND METHODS OF USE

[76] Inventors: Pravin Mishra, 3303 W. Reservoir Blvd., Peoria, Ill. 61615; John Lehmann, 486 Church Rd., Devon, Pa. 19333; Somnath Nair, 5 Oakwood Pl., Voorhees, N.J. 08043

[21] Appl. No.: 250,121
[22] Filed: May 27, 1994
[51] Int. Cl.⁶ .......................... A61M 1/00; A61B 5/00
[52] U.S. Cl. ..................... 604/29; 128/632; 128/768
[58] Field of Search ..................... 604/26–29, 604/43, 93, 96, 264; 606/108, 193, 195; 128/632, 760, 768, 769

[56] References Cited

U.S. PATENT DOCUMENTS

| | | | |
|---|---|---|---|
| 2,936,761 | 5/1960 | Snyder | 604/96 |
| 3,995,623 | 12/1976 | Blake et al. | |
| 4,072,146 | 2/1978 | Howes | |
| 4,235,231 | 11/1980 | Schindler et al. | 604/43 |
| 4,274,417 | 6/1981 | Delpy | 128/632 |
| 4,406,656 | 9/1983 | Hattler | |
| 4,437,856 | 3/1984 | Valli | 604/29 |
| 4,516,580 | 5/1985 | Polyani | 128/632 |
| 4,623,329 | 11/1986 | Drobish et al. | |
| 4,645,494 | 2/1987 | Lee et al. | |
| 4,694,832 | 9/1987 | Ungerstedt | 128/632 |
| 4,850,373 | 6/1989 | Zatloukal et al. | |
| 4,894,057 | 1/1990 | Howes | |
| 4,901,727 | 2/1990 | Goodwin | 604/43 |
| 4,903,707 | 2/1990 | Knute et al. | |
| 4,931,049 | 6/1990 | Klimas | |
| 4,994,072 | 2/1991 | Bhate et al. | |
| 5,024,654 | 6/1991 | Tyler | |
| 5,106,365 | 4/1992 | Hernandez | 604/27 |
| 5,191,898 | 3/1993 | Millar | |
| 5,191,900 | 3/1993 | Mishra | 604/29 |
| 5,207,640 | 5/1993 | Hattler | 604/28 |
| 5,212,527 | 6/1993 | Beck | |
| 5,254,084 | 10/1993 | Geary | 604/29 |
| 5,342,385 | 8/1994 | Norelli et al. | 606/193 |

OTHER PUBLICATIONS

Obrenovitch, et al., "Combined Intracerebral Microdialysis and Electrophysiological Recording: Methodology and Applications," *Journal of Neuroscience Methods*, vol. 47 (1993), pp. 139–145.

Yadid, et al., "Modified Microdialalysis Probe for Sampling Extracellular Fluid and Administering Drugs In Vivo," *American Journal of Physiology*, vol. 265 (1993), pp. R1205–R1211.

*Primary Examiner*—C. Fred Rosenbaum
*Assistant Examiner*—Frank Wilkens, III
*Attorney, Agent, or Firm*—Caesar, Rivise, Bernstein, Cohen & Pokotilow, Ltd.

[57] ABSTRACT

A microdialysis probe arranged to have a primary probe, e.g., an electrical probe, secured to it so that the microdialysis probe extends about and is concentric with the primary probe to enable the combined microdialysis probe and the primary probe to be extended as a unit through a common opening into the body of a living being, whereupon the microdialysis probe can be used for selective sampling and/or administration of dialyzable compounds in biological fluids from living tissue within the body of the being and the primary probe can be used for some other function within the body of the being without appreciably injuring adjacent tissue. The microdialysis probe comprises a tube having a lumen therethrough for releasably mounting the primary probe, and at least one dialysis chamber. In one embodiment only a single annular dialysis chamber is provided with the lumen mounting the primary probe extending therethrough. In another embodiment two semi-annular dialysis chambers are provided adjacent each other with the lumen mounting the primary probe extending therethrough. In either case each dialysis chamber comprises a wall formed of a semi-permeable material, an inlet passageway to the chamber and an outlet passageway from the chamber.

30 Claims, 4 Drawing Sheets

MICRODIALYSIS PROBES AND METHODS OF USE

BACKGROUND OF THE INVENTION

This invention relates generally to invasive medical devices and more particularly to flexible instruments designed to enter the living tissue to make measurements, deliver drugs and/or selectively sample or alter the chemical environment or analysis inside or outside of the body, and more particularly to a microdialysis probe suitable for connection to another primary probe to be extended through a common opening into the body of a living being.

Biological fluids contained in the interstitial space of tissues are often sampled for research and diagnostic purposes. Also, it is often required that the chemical composition of the interstitial space be altered via pharmacological or physiological means. Microdialysis, which employs an invasive semipermeable membrane at the end of two open ducts makes it possible to selectively sample or deliver low molecular weight substances to the interstitial space.

In U.S. Pat. No. 4,694,832 (Ungerstedt) there is disclosed a method for building a dialysis probe intended for insertion in biological tissues, for example brain tissue, containing a dialysis membrane and ducts for flow of the perfusion fluid over the membrane, and containing supports for the membrane and ducts. The probe described requires the existence of a support structure for the ducts and membrane, and thus requires its own entry port and produces its own track or laceration of the tissue as it descends into the tissue being analyzed.

In U.S. Pat. No. 5,191,900 (Mishra) there is disclosed an alternate method of fabrication of a dialysis probe, which makes use of a U-shaped loop that uses an internal, biologically inert wire combined with internal hydrostatic pressure to support the dialysis membrane and ducts. Alternative side-by-side and concentric probe configurations are also described, which exploit similar principles for support of the dialysis membrane and ducts. The Mishra '900 patent thus describes a dialysis probe which also requires its own entry port and/or the making of a separate track or laceration to enter the tissue which is to be analyzed.

As will be appreciated by those skilled in the art the use of the probes of the above two patents require the dedication of an entry port and/or the creation of a track or laceration for the dialysis probe itself. Thus, if either of these probes is to be used with another probe, i.e., a primary probe of a different type, e.g., an electrical probe, two bores will have to be provided in patient's skull, one for each probe. These limitations may be minor hindrances in some cases, e.g., blood sampling, or may be prohibitive in other cases, e.g., brain surgery, since the brain is not capable of regenerating injured or destroyed tissue. Moreover, these limitations apply whether the probe is to be used for analytical/diagnostic purposes or for therapeutic purposes. Thus, while the microdialysis probes of the above mentioned patents are suitable for their intended purposes they leave something to be desired from the standpoint of functionality.

Other probes are disclosed in U.S. Pat. Nos. 4,903,707 (Kunte), 4,931,049 (Klimas) and 5,106,365 (Hernandez).

Since the present commercially available microdialysis probes use a dedicated port of entry, they suffer from another disadvantage in order to be useful for clinical purposes; they can only be used in their miniature versions which are intended to be used primarily in rodents. The maximum surface areas and flow rates they allow coupled with the present analytical sensitivities limit their use for sampling only; that too with a poor temporal resolution. The existing microdialysis probes allow very low flow rates (0.5 to 5 ul per minute) in order to achieve reasonably high (5% to 30%) efficiency of capture of tissue analytes. This low rate is required because otherwise, there is a non-negligible depletion from the small amount of tissue surrounding the dialysis probe. Since preceding designs of dialysis probes have surface areas of about 3.8 $mm^2$, there is a small amount of tissue surface to cope with the flow volume. In the existing devices, typically, dialysates are collected at a flow rate of 0.5-5 ul/min for 10-60 min and then analyzed. The low collected quantities of these chemical are insufficient for any on-line analysis in real time for most interstitial chemicals. Constructing the prior art probes in relatively larger dimensions would eliminate some of these problems but the most common application of microdialysis being in brain tissue, having a laceration of larger magnitude in the brain to achieve these goals represents a major disadvantage, at least until there is a demonstrated evidence of any improvement in patient outcome associated with the use of these probes.

It should be noted that there is a suggestion in the prior art to the use of a microdialysis probe joined with another component for performing microdialysis and another function via a common entrance port. For example, in an article entitled Modified Microdialysis Probe For Sampling Extracellular Fluid And Administering Drugs In Vivo, by G. Yadid, K Pacak, I. J. Kpoin, and D. S. Goldstein, appearing in American Journal Of Physiology, Volume 265, 1993, pages R1205–R1211, there is disclosed a microdialysis probe having a cannula glued to its external surface to enable the administration of a pharmacological agent, glycine, through the cannula to evaluate the behavioral effect thereof on the subject, e.g., conscious rats.

In an article entitled Combined Intracerebral Microdialysis And Electrophysiological Recording: Methodology and Applications, by T. P. Obrenovitch, D. A. Richards, G. S. Sarna, and L. Symon, in the Journal Of Neuroscience Methods, Volume 47, pages 139–145, 1993, there is disclosed a microdialysis probe including in its housing a chlorided silver wire electrode for electrophysiological recording. That probe also only needs a single access port. The electrophysiological measurements, e.g., EEG and DC potentials, are obtained by the device by measuring the potential between its chlorided silver electrode and a remotely placed Ag/AgCl reference electrode.

As should be appreciated by those skilled in the art the microdialysis probes disclosed in the two above mentioned articles are integrated devices, that is the probe and the other component, be it a cannula or an electrode, are permanently secured to the probe and form a part of the probe. Hence, such devices are of limited utility and cannot be used for a wide variety of applications. Moreover, the combined structures are somewhat bulky and could result in excessive damage to adjacent tissue upon the introduction thereof into the being's body, e.g., the brain. Thus, a need still exists for a combination microdialysis probe and a primary probe of any type, and which combination will not result in excessive damage to adjacent tissue.

OBJECTS OF THE INVENTION

Accordingly, it is a general object of this invention to provide a microdialysis probe and method of use which overcomes the disadvantages of the prior art.

It is a further object of this invention to provide a combined microdialysis probe and a primary probe of any suitable type so that only a relatively small, single entry port need be provided into the patient's body for the microdialysis probe and the associated primary probe.

It is a further object of this invention to provide a microdialysis probe which is constructed to releasably receive any one of various types of other primary probes so that the microdialysis probe extends concentrically about the primary probe, whereupon only a small, single entry port need be provided into the patient's body for the introduction of the microdialysis probe and the primary probe.

SUMMARY OF THE INVENTION

These and other objects of this invention are achieved by providing a microdialysis probe arranged to have a primary probe secured to it so that the microdialysis probe extends about and is concentric with the primary probe to enable the combined microdialysis probe and the primary probe to be extended as a unit through a common opening into the body of a living being, whereupon the microdialysis probe can be used for selective sampling and/or administration of dialyzable compounds in biological fluids from living tissue within the body of the being and the primary probe can be used for some other function within the body of the being without appreciably injuring adjacent tissue.

The microdialysis probe comprises lumen means for mounting, e.g., releasably mounting, the primary probe to it, a dialysis chamber having a wall formed of a semi-permeable material having a pore size larger than the molecular weight of the dialyzable compounds, an inlet passageway to the chamber and an outlet passageway from the chamber.

The dialysis chamber is elongated and has a longitudinal axis, a distal end portion and a proximal end portion. The lumen has a longitudinal axis extending parallel to the axis of the dialysis chamber and is sized to accommodate the primary probe therein.

In accordance with one aspect of this invention the dialysis chamber is of annular shape and has an inner cylindrical wall which forms the primary probe receiving lumen. The outer wall of the dialysis chamber is formed of the semi-permeable material.

In accordance with another aspect of this invention the microdialysis probe comprises a pair of dialysis chambers. Each of the chambers has an outer wall formed of a semi-permeable material and respective inlet and outlet passageways coupled to the interior of respective ones of the pair of chambers. Each of the dialysis chambers is elongated and of semi-annular shape having a longitudinal axis, a distal end portion and a proximal end portion. The means for mounting the primary probe to the microdialysis probe comprises a common lumen having a longitudinal axis extending parallel to the axes of the two semi-annular chambers, with the common lumen being sized to accommodate the primary probe therein.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENT

Figure 1:
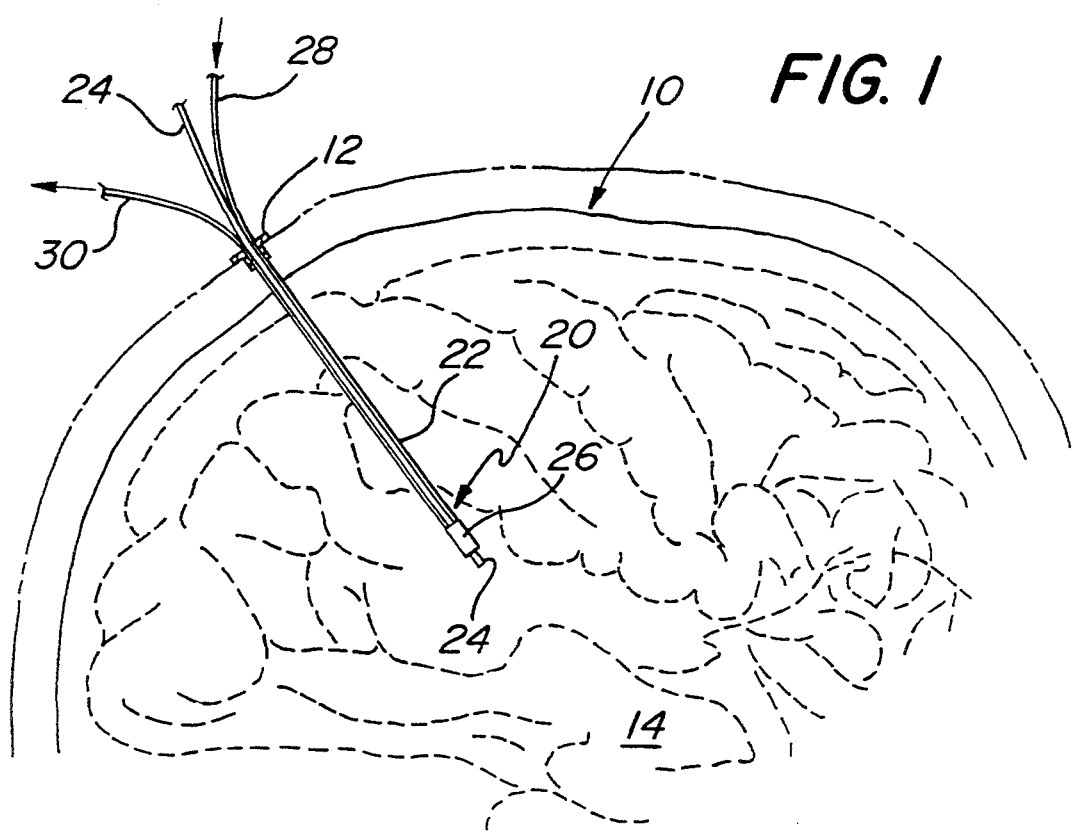
FIG. 1 is a side elevational view, not to scale, showing one embodiment of a microdialysis probe constructed in accordance with this invention extending through a single entry port in the skull so that the microdialysis chamber and the primary probe are both located within the brain of a living being.
Figure 4:
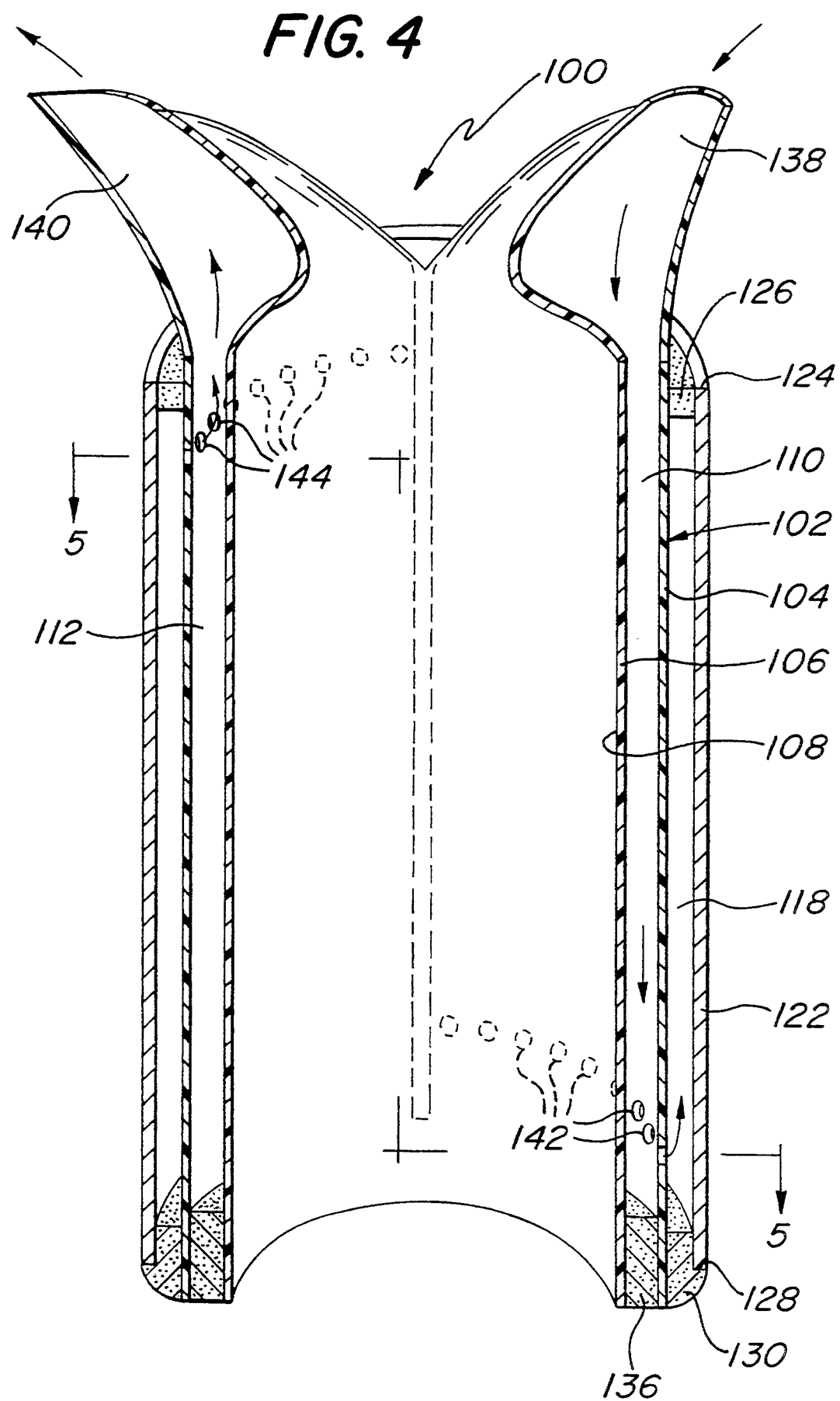
FIG. 4 is a view similar to that of FIG. 2 but showing the distal end of an alternative embodiment of a microdialysis probe constructed in accordance with this invention.
Figure 5:
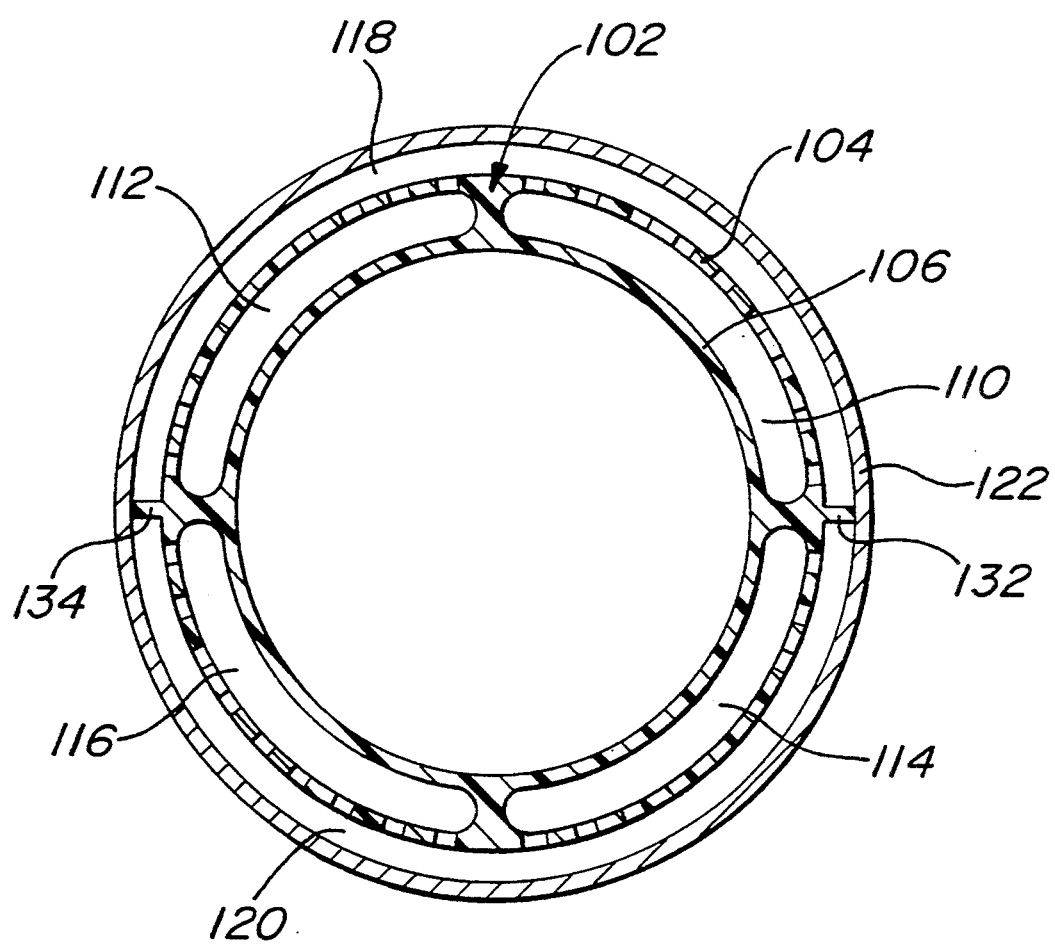
FIG. 5 is a sectional view taken along lines 5-5 of FIG. 4.

Referring now to the various figures of the drawing wherein like reference characters refer to like parts, there is shown at 20 in FIG. 1, one embodiment of a microdialysis probe constructed in accordance with this invention shown in position extending through the skull 10 of a person so that the distal end of the probe is located within the person's brain 14. In FIGS. 4 and 5 there is shown the distal end of another microdialysis probe 100 (to be described later. This alternative probe is arranged to be used in the same manner as probe 20.

It should be pointed out at this juncture that the most eminent use of microdialysis probes constructed in accordance with this invention is in sampling and or altering the chemical environment of the brain. Thus, the probe 20 is shown in an exemplary position passing through a conventional access port 12 in the skull 10 and into the brain 14. However the probes 20 and 100 may also be used for similar purposes in other tissues or tissue matrices of the body. In particular, the probes 20 and 100 can be used for sampling the chemical environment of blood, muscle, skin, amniotic fluid, and other organs and components of the body. To that end, the probes 20 and 100 are arranged to allow the introduction of compounds of low molecular weight in the specific sites of the tissue while collecting samples, and thus enable monitoring the effects produced by the substance introduced in the fully interactive living biological system.

Figure 3:
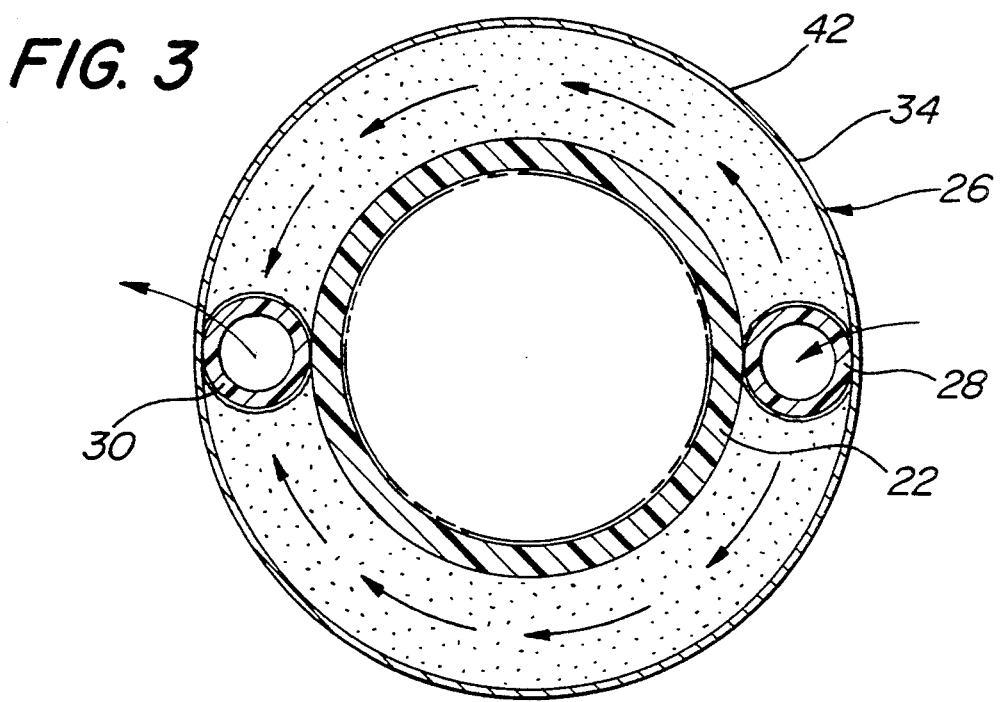
FIG. 3 is a sectional view taken along lines 3-3 of FIG. 2.
Figure 2:
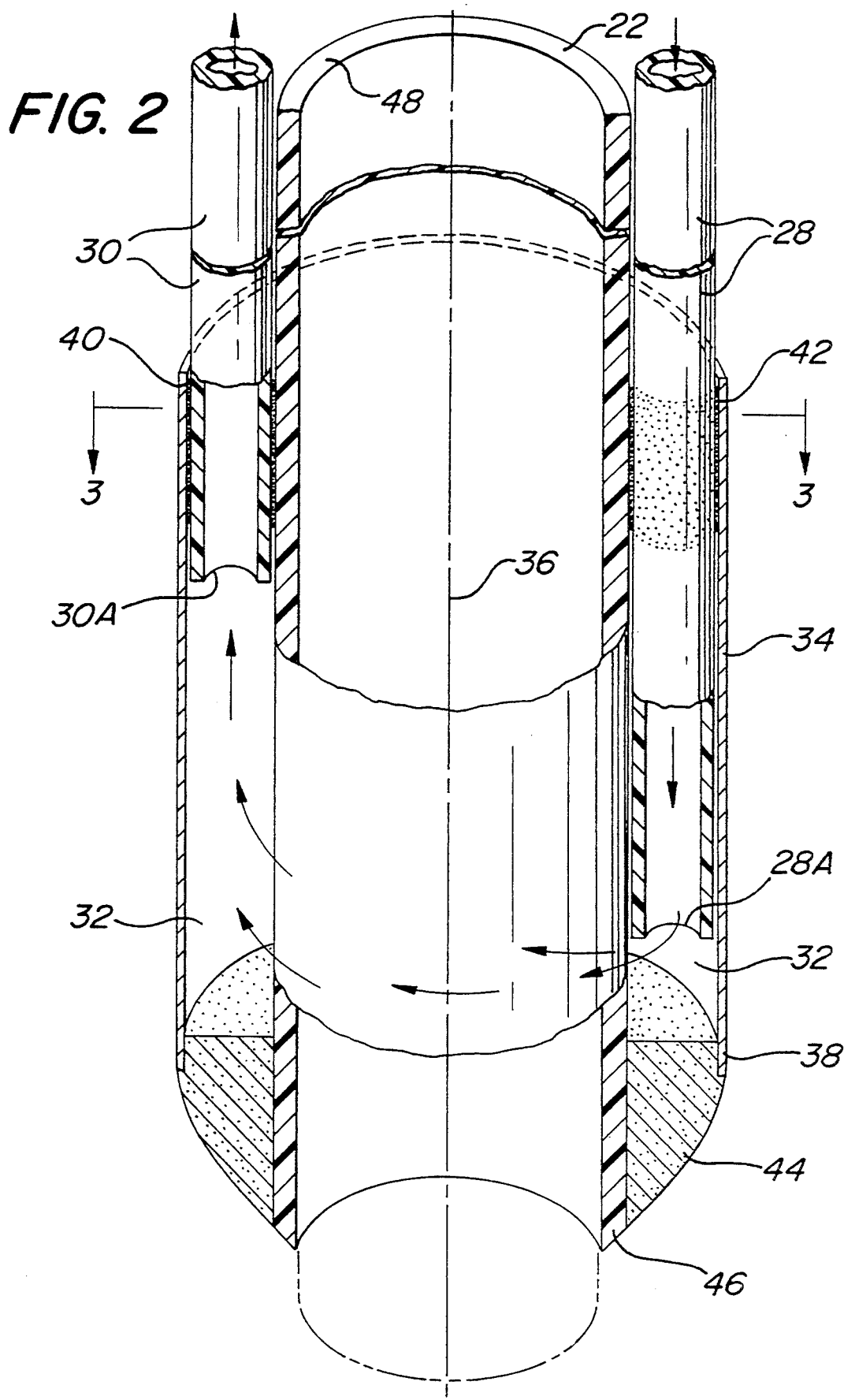
FIG. 2 is a greatly enlarged isometric view, partially in section of the distal end of the embodiment of a microdialysis probe shown in FIG. 1.

As can be seen in FIGS. 2-3, the probe 20 basically comprises an elongated central tube 22 which is arranged to receive in its central passageway or lumen any type of primary device, e.g., a primary probe 24, such as an indwelling catheter, a biopsy needle, an intercranial pressure monitor, or an electrophysiological probe, to have access to the specific internal site at which the microdialysis probe 20 will be located. The tube 22 is constructed of a biologically inert plastic or other similar material, such as polyamide or polyester, that is strong enough to accommodate the range of fluid pressures that the circulating dialysis solution may exert, at extremely thin wall configurations.

An annular dialysis chamber 26 is mounted on the distal end of the central tube 22. At least one fluid inlet tube 28 and at least one fluid outlet tube 30 communicate with the interior 32 of the dialysis chamber. The dialysis chamber includes a cylindrical outer wall 34. This wall is made up of semi-permeable membrane having a pore size larger than the molecular weight of the dialyzable compounds. The semi-permeable membrane extends concentrically about and somewhat close to the outer periphery of the distal end of the central tube 22 to form the dialysis chamber therebetween. The fluid inlet tube comprises an elongated tube whose external diameter is just slightly less than the thickness of the annular dialysis chamber. The fluid outlet tube also comprises an elongated tube whose external diameter is just slightly less than the thickness of the annular dialysis chamber.

As can be seen in FIG. 3 the distal end portion of the inlet tube 28 extends along the outer surface of the central tube 22 parallel to the longitudinal central axis 36 thereof so that the inlet tube's open free end 28A is located within and closely adjacent the bottom or distal end 38 of the annular dialysis chamber and is in fluid communication with the interior of the dialysis chamber. The distal end portion of the outlet tube 30 also extends along the outer surface of the central tube 22 parallel to the longitudinal axis 36 but on the opposite side as the inlet tube 28 so that the open free end 30A of the outlet tube is located within the dialysis chamber closely adjacent the top or proximal end 40 thereof and in fluid communication with the interior of the dialysis chamber.

The proximal end 40 of the semi-permeable membrane of the dialysis chamber is fixedly secured about its entire periphery to the outer surface of the immediately adjacent portion of the central tube 22 by means of any suitable adhesive or glue 42, e.g., epoxy or cryanoacrylate, extending between those surfaces. The inlet and outlet tubes 28 and 30, respectively, pass through the adhesive 42 so that their open ends are located within the dialysis chamber as described heretofore. The adhesive also serves to hold the inlet and outlet tubes in their desired positions therein.

In a similar manner the distal end of the semi-permeable membrane of the dialysis chamber is fixedly secured about its entire periphery to the outer surface of the central tube 22 by any suitable adhesive or glue 44 extending between those surfaces. As can be seen in FIG. 2, the adhesive or glue 44 is disposed in a ring which includes an outer surface which tapers arcuately from the outer surface of the semi-permeable membrane until it merges with the tapering distal free edge 46 of the central tube 22. The tapering surface of the glue 44 ensures that tissue damage is kept to a minimum when the probe is inserted into the brain.

The inlet tube 28 conducts the dialysis medium, consisting of ingredients selected either for minimal perturbation of the chemical environment, or consisting of compounds added either for diagnostic, analytical, or therapeutic applications into the interior of the microdialysis chamber 32. In accordance with a preferred embodiment of this invention the entry and exit tubes 28 and 30, respectively, are made of polyamide, fused silica, or other materials consistent with the objectives of resistance to high internal and/or external pressures, small size, and biological inertness. Each tube is of sufficient length to reach outside of the tissue entry port. The inlet tube is preferably attached to a liquid pump (not shown). That pump may be a mechanically driven syringe pump and is coupled to the inlet tube 28 with a luer-lock fitting (not shown), with or without adapters, such as polyethylene tubing. This arrangement enables the pump to deliver the microdialysis medium to the bottom of the microdialysis probe.

As can be seen clearly in FIG. 2, the distal end 28A of the entry tube 28 and the distal 30A of exit tube 30 are situated preferably farthest from each other in order to allow a maximum circulation of the fluid within the chamber 32. This action allows maximum efficacy of the solute exchange. The direction of flow of the fluid through the tubes and microdialysis chamber is shown by the arrows in FIGS. 2 and 3.

Both the entry and exit tubes 28 and 30 respectively, are selected and designed such that they pass through the access port 12. That port may be any suitable conventional component such as is available from various manufacturers, e.g., Camino Laboratories, Inc., for the purpose of inserting the primary invasive device(s) through a common entry site. The exit or outlet tube 30 serves as the means to collect the microdialysis medium from the probe's chamber 32 once the analytes of interest have diffused across the dialysis membrane, and thus serves as an egress for the microdialysis medium from the probe. To that end, the exit tube 30 is of such a length as to remove the microdialysate outside the tissue to a point where it can be collected.

The primary purpose of the central tube's lumen 22 is to serve as a passage for the releasable mounting of a primary invasive device e.g., a probe 24, or any other device (not shown). The central lumen can also be used to receive a rigid stylet (not shown) in the event that no primary device is intended for use. The inner diameter of the lumen can be fabricated either to fit tightly (i.e., press fit) or loosely (i.e., slip-fit) the primary invasive device. When the lumen is sized to allow the slip-fitting of the primary devices therein, the depth of penetration of the microdialysis probe 20 and the primary probe or device 24 can be independently adjusted.

In some instances the central tube 22 may replace the sheath that is used to protect the delicate cable or equivalent of the primary invasive device. In these circumstances, the cable of the primary invasive device would be considered as primary invasive device.

The semi-permeable membrane serves the primary function of creating a fluid compartment within the fluid matrix of a tissue, such as brain, and allows only passive diffusion of small molecular weigh solutes across its pores. To that end the microdialysis membrane may be made from regenerated cellulose and having a permeability limit such as 6000 Dalton. With this material molecules with molecular weight greater than 6000 Dalton will not pass therethrough, whereas molecules of less than 6000 Dalton will pass therethrough. Other materials besides regenerated cellulose may be used, and other cut-offs different from 6000 Dalton may be used, to permit the dialysis of molecules of different molecular species. However, it is imperative that the dialysis membrane used must be capable of withstanding pressures created by fluid flow within and pressure exerted by the tissue environment, such as intracranial fluid. Regenerated cellulose membranes are used in the preferred embodiment since such materials will withstand pressures up to 610 mm Hg, approximately three times higher than the highest intracranial pressure to be encountered.

The central tube 22 may be of any suitable length so that its top edge 48 (FIG. 2) is located adjacent the entry port 12 through the skull. In accordance with a preferred embodiment of the invention, the inlet and outlet tubes 28 and 30 extend along and are secured to the outer surface of the central tube 22 by securement means, e.g., an adhesive, (not shown). This arrangement ensures that the inlet and outlet tubes do not cause damage to adjacent tissue, as could occur if the probe 20 was extended through an arcuate path or track into the brain. In such a case, if the inlet and outlet tubes did not extend along the central tube they could take a different track through the brain than the central tube 22 thus damaging adjacent tissue.

In FIGS. 4 and 5 there is shown the distal end of the alternative embodiment 100 of a microdialysis probe of this invention. The probe 100 includes two microdialysis chambers to permit simultaneous perfusion of the two chambers under different conditions, e.g., flow rate, medium composition. Thus, one dialysis function, e.g., a diagnostic function, can be carried out in one chamber, and a second dialysis function, e.g., a therapeutic function can be carried out in the other chamber at the same time.

The probe 100 basically comprises a dual walled tube 102 having an outer wall 104 and an inner wall 106. The tube 102 is preferably formed of the same material as that of the tube 22 of the probe 20 described heretofore. The inner wall 106 includes a central passageway 108 extending through it for receipt of the primary probe 24.

As can be seen clearly in FIG. 5, four passageways 110, 112, 114, and 116 extend through the dual walled tube 102. Each of the passageways extends for approximately ninety degrees of the circumference of the dual walled tube. The passageways 110 and 112 from the inlet and outlet, respectively, to a first microdialysis chamber 118, while the passageways 114 and 116 from the inlet and outlet of the second microdialysis chamber 120.

The microdialysis chambers 118 and 120 are each semi-annular in shape and are formed by a common cylindrical outer wall 122 of the same semi-permeable material as the outer wall 34 of the probe 20. The cylindrical outer wall 122 extends concentrically about the outer wall 104 of the dual walled tube 102, and is spaced slightly therefrom to define the two chambers 118 and 120 therebetween. The outer wall 122 is secured in place about its top peripheral edge 124 by a ring of glue 126 of the same composition as that described heretofore. In a similar manner the bottom peripheral edge 128 of the semipermeable membrane outer wall 122 is secured in place by a ring of glue 130, which is also of the same composition as that described heretofore.

The dual walled tube 102 includes a pair of longitudinally extending ribs 132 and 134 (FIG. 5) projecting out of the outer surface of the dual walled tube 102. These ribs are located diametrically opposite each other, with rib 132 being located at the interface of passageways 110 and 114 and with rib 134 being located at the interface of passageways 112 and 116. The ribs are each of a height equal to the distance separating the inner surface of the semipermeable outer wall 122 and the outer surface of the dual walled tube so that they divide the space between the outer wall 122 and the dual walled tube into the two semi-annular chambers 118 and 120.

The bottom of each of the passageways 110, 112, 114 and 116 is sealed by a plug of glue 136 of the same type as described earlier. The top of each of the passageways terminates in a conduit. In particular, the inlet passageway 110 to microdialysis chamber 118 terminates in a conduit 138 while the outlet passageway 112 to that chamber terminates in a conduit 140. In a similar manner the passageways 114 and 116 to and from the other microdialysis chamber 120 terminate in respective conduits (not shown).

The passageway 110 communicates with the bottom of the microdialysis chamber 118 via a plurality of holes or apertures 142, while the passageway 112 communicates with the top of that microdialysis chamber via a plurality of holes or apertures 144. Thus, a microdialysis medium may be pumped from a pump (not shown) connected to the inlet conduit 110, whereupon that medium will flow through the inlet conduit 138 into the communicating passageway 110 through the apertures 142 into the bottom of the microdialysis chamber 118, through that chamber out of the apertures 144 into the passageway 112 and from there through the outlet conduit 140 in the direction of the arrows shown in FIG. 4. Another microdialysis medium may be pumped from another pump (not shown) into the inlet conduit connected to passageway 114 to the microdialysis chamber 120 in a similar manner. That medium will then pass out of the chamber 120 into the passageway 116 and the communicating outlet conduit.

As should be appreciated by those skilled in the art, the microdialysis probe 100, in addition to providing a pair of microdialysis chambers 118 and 120, also provides for the transport of the dialysis medium to and from those chambers via internally located passageways, i.e., the passageways in the dual walled tube 102. That dual walled tube can be readily fabricated, e.g., extruded from any suitable material, e.g., polyester, polyamide or TEFLON ®.

It should be pointed out at this juncture that a microdialysis probe can be constructed to incorporate more than the two microdialysis chambers shown in the embodiment 100.

As should now be appreciated by those skilled in the art, the probes 20 and 100 of this invention provides an additional capability, namely, microdialysis, to the capability of the primary device with minimal increase in diameter over that of the primary device. Further still the probes 20 and 100 do not require an independent access port other than port 12, or make a separate track or laceration through the tissue being sampled, analyzed or treated. Thus, the subject invention eliminates most, if not all, of the problems the prior art set forth above and offers much greater adaptability in order to be suitable for several possible applications.

In accordance with one preferred embodiment of this invention, the microdialysis probes 20 and 100 are sufficiently small, e.g., have an external diameter of 4 mm and a length of at least 30 mm, to enable each to be accommodated within a conventional skull access port, giving a surface area of 377 square millimeters. This area is approximately 100 to 300 times greater than the prior art dialysis probes. Accordingly, microdialysis probes constructed in accordance with this invention can provide a flow rate approaching 100 ul/minute without sacrificing efficiency or adversely depleting interstitial space of chemicals needed for maintaining tissue viability.

Some exemplary advantages of such a configuration are: In a situation where only partial sampling of interstitial chemicals is desired and larger depletion of these chemicals is undesirable, one can use extremely low flow rates (1–4 ul/min) achieving 80–100% efficacy. The increased surface area of the probes 20 and 100 also translate into a reduction in variability, over time and from patient to patient, because of the greater amount of tissue which is sampled. In a situation where a fast depletion of endogenous toxins is desired, a very high flow rate can be used by properly choosing the configuration. For example, the probes 20 or 100 may be used to remove water, in the case of edema, by dialyzing a hypertonic Dextran solution of a molecular weight of 100,000 Dalton, or to remove ammonia, in the case of acute liver failure. In these therapeutic applications, it is possible to superfuse at significantly higher flow rates, e.g., 1 ml/min or higher. This means that greater amounts of toxic substances can be removed from the tissue when the patient's vasculature is unable to do so, e.g., because of pathologically high intracranial pressure which pinches shut the venous outflow, or because of pathologically high levels of ammonia in the blood.

In a setting where a pharmaceutical agent is to be dialyzed out, a greater surface area can be exposed at low, medium or high flow rate, depending on whether or not a simultaneous sampling of its effects on interstitial chemistry is desired. The concentration of the infused drug can be easily adjusted and adapted according to flow rate to get the maximum therapeutic advantage. All of these advantages are obtained from a larger size dialysis probe, without any significant increase in the amount of tissue damage over the size of the primary probe.

The primary probe, with which the microdialysis probes 20 and 100 of this invention can be used, can comprise any conventional device, such as an intracranial pressure probe, an electrophysiological recording electrode, standardized disposable surgical instruments (e.g., a spinal needle, such as a luer-lock syringe tip or cannula, usually having a beveled and sharp tip), etc. Moreover, it is possible to easily adapt the microdialysis probe described here to multiple types of primary probes, the diameter of the primary probe being the only parameter of significance to change, from the perspective of the microdialysis probe. In cases where no primary probe is intended for use, a structure, such as a stylet or a beveled cannula, may be selected based purely on considerations for delivery (cutting or blunt, flexible or rigid, plastic or steel), and can be obtained economically and readily, to be used as the primary probe for delivery purposes.

As should be appreciated from the foregoing the subject invention provides a microdialysis probe which can use, either simultaneously or independently, the same entry and passage as that used by other invasive devices; thus minimizing or eliminating an increased possibility of infection due to use of the microdialysis probe, and minimizing or eliminating increased tissue damage caused by the physical insertion of the probe is described. Thus, the subject invention provides the clinician or scientific researcher with a means of performing microdialysis via a single entry passage in the body along with use of one, or more other invasive devices. This arrangement of microdialysis probe with other invasive devices offers maximal flexibility in logistic terms, i.e., the potential to stock primary probes separately from microdialysis probes and use the combined configuration at the physician's option; and to adjust the depth of the two probes independently. Most importantly, it offers methods for sampling and therapeutically modifying the chemical environment of tissue with minimal invasiveness.

Without further elaboration, the foregoing will so fully illustrate our invention that others may, be applying current or future knowledge, adopt the same for use under various conditions of service.

We claim:

1. A microdialysis probe arranged to have a primary probe releasably secured to it to enable the microdialysis probe and the primary probe to be extended as a unit through a common opening into the body of a living being, whereupon the microdialysis probe can be used for selective sampling and/or administration of dialyzable compounds in biological fluids from living tissue within the body of the being and the primary probe can be used for some other function within the body of the being, said microdialysis probe comprising means for releasably mounting said primary probe to said microdialysis probe, a dialysis chamber having a wall formed of a semi-permeable material having a pore size larger than the molecular weight of the dialyzable compounds, an inlet passageway to said chamber and an outlet passageway from said chamber.

2. The microdialysis probe of claim 1 wherein said dialysis chamber is elongated and has a longitudinal axis, a distal end portion and a proximal end portion, and wherein said means for mounting said primary probe comprises a lumen having a longitudinal axis extending parallel to the axis of said chamber, said lumen being sized to accommodate said primary probe therein.

3. The microdialysis probe of claim 2 wherein said dialysis chamber is of annular shape and has an inner cylindrical wall, and wherein said wall of said semipermeable material comprises an outer wall of said annular shaped dialysis chamber, said inner wall defining said lumen therein.

4. The microdialysis probe of claim 3 wherein the inner wall extends through at least the entire length of said outer wall of said annular microdialysis chamber.

5. The microdialysis probe of claim 3 wherein said inner wall of said chamber has a proximal end portion and wherein said outer wall of said chamber has a proximal end portion, with said proximal end portion of said inner wall extending in the proximal direction substantially beyond the proximal end portion of said outer wall.

6. The microdialysis probe of claim 5 wherein said inlet passageway and said outlet passageway each include a distal portion located within said chamber and proximal portion located outside said chamber, said proximal portions of said passageways extending parallel to the longitudinal axis of said inner wall along said proximal portion of said inner wall.

7. The microdialysis probe of claim 2 wherein said inlet passageway is an elongated tubular member having a distal end including a opening and a proximal end including an opening, said distal end opening of said inlet passageway being located within said distal portion of said dialysis chamber, said proximal end opening of said inlet passageway being located outside of said dialysis chamber substantially beyond its proximal end portion.

8. The microdialysis probe of claim 2 wherein said outlet passageway is an elongated tubular member having a distal end including a opening and a proximal end including an opening, said distal end opening of said outlet passageway being located within said proximal portion of said dialysis chamber, said proximal end opening of said outlet passageway being located outside of said dialysis chamber substantially beyond its proximal end portion.

9. The microdialysis probe of claim 7 wherein said outlet passageway is an elongated tubular member having a distal end including a opening and a proximal end including an opening, said distal end opening of said outlet passageway being located within said proximal portion of said dialysis chamber, said proximal end opening of said outlet passageway being located outside of said dialysis chamber substantially beyond its proximal end portion.

10. The microdialysis probe of claim 9 wherein said distal opening of said inlet passageway is located in a diametrically opposed side of said dialysis chamber from said distal opening of said outlet passageway.

11. The microdialysis probe of claim 1 wherein said probe comprises a pair of dialysis chambers, and wherein each of said chambers has a wall formed of a semi-permeable material, and respective inlet and outlet passageways coupled to the associated chamber.

12. The microdialysis probe of claim 11 wherein each of said dialysis chambers is elongated and of semi-annular shape having a longitudinal axis, a distal end portion and a proximal end portion, and wherein said means for mounting said primary probe comprises a common lumen having a longitudinal axis extending parallel to the axes of said semi-annular chambers, said common lumen being sized to accommodate said primary probe therein.

13. The microdialysis probe of claim 12 wherein said wall of said semi-permeable material makes up the outer walls of both of said semi-annular chambers, said common lumen defining a common inner wall for each of said semi-annular chambers.

14. The microdialysis probe of claim 13 wherein the inner wall extends through at least the entire length of said outer wall of said semi-annular chamber.

15. The microdialysis probe of claim 13 wherein said inner wall has a proximal end portion and wherein said outer wall has a proximal end portion, with said proximal end portion of said inner wall extending in the proximal direction substantially beyond the proximal end portion of said outer wall.

16. The microdialysis probe of claim 15 wherein the inlet passageway and the outlet passageway to one of said semi-annular chambers each include a distal portion located within said one semi-annular chamber and proximal portion located outside said one semi-annular chamber, with said proximal portions of said passageways extending parallel to the longitudinal axis of said inner wall along said proximal portion of said inner wall, and wherein the inlet passageway and the outlet passageway to the other of said semi-annular chambers each include a distal portion located within said other semi-annular chamber and proximal portion located outside said semi-annular chamber, with said proximal portions of said passageways extending parallel to the longitudinal axis of said inner wall along said proximal portion of said inner wall.

17. The microdialysis probe of claim 12 wherein each of said inlet passageways is an elongated tubular member having a distal end including a opening and a proximal end including an opening, said distal end opening of one of said inlet passageway being located within the distal portion of one semi-annular chamber, said proximal end opening of said one inlet passageway being located outside of said one semi-annular chamber substantially beyond the proximal end portion of said one semi-annular chamber, said distal end opening of the other of said inlet passageway being located within the distal portion of the other semi-annular chamber, said proximal end opening of said other inlet passageway being located outside of said other semi-annular chamber substantially beyond the proximal end portion of said other semi-annular chamber.

18. The microdialysis probe of claim 12 wherein each of said outlet passageways is an elongated tubular member having a distal end including a opening and a proximal end including an opening, said distal end opening of one of said outlet passageways being located within the proximal portion of one semi-annular chamber, said proximal end opening of said one outlet passageway being located outside of said one semi-annular chamber substantially beyond the proximal end portion of said one semi-annular chamber, said distal end opening of the other of said outlet passageways being located within the proximal portion of the other semi-annular chamber, said proximal end opening of said other outlet passageway being located outside of said other semi-annular chamber substantially beyond the proximal end portion of said other semi-annular chamber.

19. The microdialysis probe of claim 17 wherein each of said outlet passageways is an elongated tubular member having a distal end including a opening and a proximal end including an opening, said distal end opening of one of said outlet passageways being located within the proximal portion of one semi-annular chamber, said proximal end opening of said one outlet passageway being located outside of said one semi-annular chamber substantially beyond the proximal end portion of said one semi-annular chamber, said distal end opening of the other of said outlet passageways being located within the proximal portion of the other semi-annular chamber, said proximal end opening of said other outlet passageway being located outside of said other semi-annular chamber substantially beyond the proximal end portion of said other semi-annular chamber.

20. A combination microdialysis probe and a primary probe arranged to be extended as a unit through a common opening into the body of a living being, whereupon the microdialysis probe can be used for selective sampling and/or administration of dialyzable compounds in biological fluids from living tissue within the body of the being and the primary probe can be used for some other function within the body of the being, said combination comprising a primary probe and a microdialysis probe comprising a central lumen for mounting said primary probe therein so that said primary probe extends through said microdialysis probe and with said microdialysis probe extending generally concentrically about said primary probe, said dialysis probe additionally comprising a dialysis chamber having an outer wall formed of a semi-permeable material having a pore size larger than the molecular weight of the dialyzable compounds, an inner wall through which said lumen extends, an inlet passageway to said chamber and an outlet passageway from said chamber.

21. The microdialysis probe of claim 20 wherein said outer wall is cylindrical and said inner wall is cylindrical, whereupon said dialysis chamber is of annular shape.

22. The microdialysis probe of claim 20 wherein the inner wall extends through at least the entire length of said outer wall of said annular microdialysis chamber.

23. The microdialysis probe of claim 22 wherein said inner wall of said chamber has a proximal end portion and wherein said outer wall of said chamber has a proximal end portion, with said proximal end portion of said inner wall extending in the proximal direction substantially beyond the proximal end portion of said outer wall.

24. The microdialysis probe of claim 23 wherein said inlet passageway and said outlet passageway each include a distal portion located within said chamber and proximal portion located outside said chamber, said proximal portions of said passageways extending parallel to the longitudinal axis of said inner wall along said proximal portion of said inner wall.

25. The microdialysis probe of claim 24 wherein said distal opening of said outlet passageway is located within a proximal portion of said dialysis chamber, and wherein said distal opening of said inlet passageway is located within a distal portion of said dialysis chamber.

26. The microdialysis probe of claim 25 wherein said distal opening of said inlet passageway is located in a diametrically opposed side of said dialysis chamber from said distal opening of said outlet passageway.

27. The microdialysis probe of claim 20 wherein said probe comprises a pair of dialysis chambers, and wherein each of said chambers has an arcuate outer wall formed of a semi-permeable material, an arcuate inner wall, and respective inlet and outlet passageways coupled to the associated chamber, said arcuate inner walls of said pair of chamber being contiguous with each other and with said lumen extending therethrough.

28. The microdialysis probe of claim 27 wherein each of said dialysis chambers is elongated and of semi-annular shape having a longitudinal axis, a distal end portion and a proximal end portion.

29. The microdialysis probe of claim 28 wherein said wall of said semi-permeable material makes up the outer walls of both of said semi-annular chambers.

30. The microdialysis probe of claim 29 wherein the inner wall extends through at least the entire length of said outer wall of said semi-annular chamber.

* * * * *